United States Patent [19]
Giudicelli et al.

[11] 3,987,177
[45] Oct. 19, 1976

[54] VINCAMINIC ACID ESTERS

[75] Inventors: Don Pierre René Lucien Giudicelli, Fontenay-sous-Bois; Henry Najer; Yves Robert Alain Pascal, both of Paris; Patrick André Louis Lardenois, Gentilly, all of France

[73] Assignee: Synthelabo, Paris, France

[22] Filed: June 20, 1975

[21] Appl. No.: 588,593

[30]     Foreign Application Priority Data
    June 27, 1974  France ............................. 74.22369

[52] U.S. Cl............................ 424/267; 260/293.53
[51] Int. Cl.².................................... C07D 401/04
[58] Field of Search................ 260/293.53; 424/267

[56]         References Cited
         UNITED STATES PATENTS

| | | | |
|---|---|---|---|
| 3,454,583 | 7/1969 | Kuehne | 260/294.3 |
| 3,755,333 | 8/1973 | Szantay et al. | 260/293.53 |
| 3,884,927 | 5/1975 | Martel et al. | 260/293.53 |
| 3,891,640 | 6/1975 | Plat et al. | 260/247.5 FP |

OTHER PUBLICATIONS

Morrison et al., "Organic Chemistry," 2nd Ed., Allyn and Bacon, Boston (1966), pp. 601–603.

*Primary Examiner*—G. Thomas Todd
*Attorney, Agent, or Firm*—Armstrong, Nikaido & Wegner

[57]          ABSTRACT

The invention provides vincaminic acid esters of formula

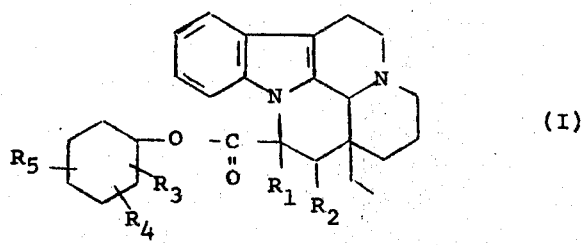

wherein $R_1$ is hydrogen or hydroxy, $R_2$ is hydrogen or $R_1$ and $R_2$ form an additional bond between the two carbon atoms to which they are attached, and $R_3$, $R_4$ and $R_5$ are hydrogen or methyl, and their salts. The esters are useful in treatment of cardiac-circulatory, cerebal-vascular or respiratory insufficiency.

13 Claims, No Drawings

VINCAMINIC ACID ESTERS

This invention relates to compounds which are vincaminic acid esters, to a process for their preparation and to pharmaceutical compositions containing them.

The esters are useful in the treatment of cardiac-circulatory, cerebal-vascular or respiratory insufficiencies.

The esters have the general formula (I)

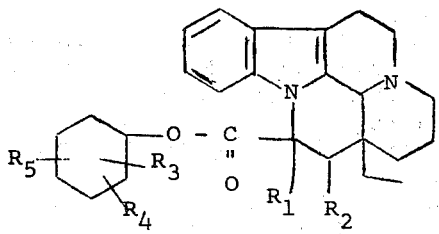

wherein
$R_1$ is a hydrogen atom or a hydroxy group;
$R_2$ is a hydrogen atom, or
$R_1$ and $R_2$ together form an additional bond between the two carbon atoms to which they are attached, and each of
$R_3$, $R_4$ and $R_5$, which may be the same or different, is a hydrogen atom or a methyl group, or a pharmaceutically acceptable acid addition salt thereof with an inorganic or organic acid.

The esters of the invention can be prepared from vincaminic acid, desoxyvincaminic acid or apovincaminic acid or a functional derivative thereof by reaction with a cyclohexane derivative. The functional derivative can be, for example, an acid halide, which can be reacted with an appropriate cyclohexanol.

The acid halides can be prepared by conventional methods, for example by converting the acid to its acid halide using an oxalyl halide or thionyl halide.

The invention is illustrated by the following Examples.

EXAMPLE 1: 3,3,5-Trimethylcyclohexyl apovincaminate and its hydrochloride

[$R_1$ and $R_2$ = a double bond; $R_3$, $R_4$ and $R_5$ = $CH_3$ in positions 3, 3 and 5; code number: SL C 072]

3 G (0.025 g.mol) of thionyl chloride are added to a mixture of 3.2 g (0.01 g.mol) of apovincaminic acid, 200 ml of dry benzene and 0.5ml of dimethylformamide and the resulting mixture is refluxed for 20 minutes, whilst stirring. It is then left overnight and the solvent is evaporated in vacuo on a waterbath. To remove thoroughly all traces of thionyl chloride, the residue is taken up 3 times in 50 ml of anhydrous benzene, the benzene in each case being driven off on a waterbath under reduced pressure. The acid chloride thus prepared is taken up in 50 ml of pyridine and 25 ml of anhydrous benzene, 2 g (0.014 g.mol) of 3,3,5-trimethylcyclohexanol are added and the mixture is refluxed whilst stirring for 1 ½ hours. The solvents are then driven off in vacuo on a waterbath and the traces of pyridine are driven off by azeotropic distillation using toluene (2 × 50 ml).

The residue is taken up in 200 ml of water and 100 ml of ether, this mixture is rendered alkaline with concentrated ammonia, and the whole mixture is stirred for 15 minutes. The organic phase is decanted, washed with water and poured into 100 ml of 1 M- hydrochloric acid, and the mixture is stirred vigorously for 1 hour. The product is filtered off, washed with water and dried to give 4 g (yield = 83%) of 3,3,5-trimethylcyclohexylapovincaminate hydrochloride Analysis: $C_{27}H_{39}N_2O_2Cl$ (m.w. 483) (This compound contains 3.67% of water as determined by the Karl Fischer method). Calculated: C, 69.47; H, 8.24; N, 5.59; Cl, 7.07%. Found: C, 69.53; H, 8.67; N, 5.59; Cl, 7.32%.

EXAMPLE 2:
3,3,5-Trimethylcyclohexyl desoxyvincaminate and its hydrochloride

[$R_1$ = $R_2$ = H; $R_3$, $R_4$ and $R_5$ = $CH_3$ in positions 3, 3 and 5; code number: SL C 084]

0.72 G (0.006 g.mol) of thionyl chloride is added to a mixture of 1.95 g (0.006 g.mol) of desoxyvincaminic acid, 80 ml of dry benzene and 0.5 g of dry pyridine, and the resulting mixture is stirred overnight at ambient temperature. The benzene is driven off in vacuo on a waterbath and the residue is freed from traces of thionyl chloride by azeotropic distillation, using dry benzene (3 × 20 ml). The acid chloride thus prepared is taken up in 60 ml of dry pyridine and 30 ml of dry benzene, 1.7 g (0.012 g.mol) of 3,3,5-trimethylcyclohexanol are added and the mixture is refluxed whilst stirring for 1 ½ hours. The solvents are driven off in vacuo on a waterbath and the traces of pyridine are removed by azeotropic distillation using toluene. The residue is taken up in 100 ml of water and 50 ml of ether and this mixture is stirred for 15 minutes; the organic phase is decanted, treated with activated vegetable charcoal and poured into 100 ml of 1 M-hydrochloric acid whilst stirring vigorously to start the crystallisation. The precipitate is filtered off, washed with water and dried to give 1.2 g (yield: 41%) of 3,3,5-trimethylcyclohexyl desoxyvincaminate hydrochloride. Melting point = 250° C.

Analysis: $C_{29}H_{41}N_2O_2Cl$ (m.w. 485) (This compound contains 1.24% of water as determined by the Karl Fischer method). Calculated: C, 70.93; H, 8.55; N, 5.71; O, 7.61 Cl, 7.22%. Found: C, 70.91; H, 8.67; N, 5.45; O, 7.76; Cl, 7.44%.

EXAMPLE 3: The methylsulphonic acid salt of 3,3,5-trimethylcyclohexyl apovincaminate

[$R_1$ and $R_2$ = a double bond; $R_3$, $R_4$ and $R_5$ = $CH_3$ in positions 3, 3 and 5; code number: SL C 135]

3.2 G (0.0072 g.mol) of 3,3,5-trimethylcyclohexyl apovincaminate are dissolved in 20 ml of dry methanol. 0.687 G (0.0072 g.mol) of methanesulphonic acid in 10 ml of anhydrous methanol are poured into this solution. The mixture is stirred for 15 minutes, the methanol is then driven off in vacuo on a waterbath and the oil obtained is dried to give the methylsulphonic acid salt of 3,3,5-trimethylcyclohexyl apovincaminate, a water-soluble compound which melts at 280° C.

Analysis: $C_{30}H_{42}N_2O_5S$ (m.w. 542.6) Calculated: C, 66.41; H, 7.81; N, 5.17; S, 5.91%. Found: C, 66.37; H, 8.02; N, 4.99; S, 5.54%.

The compounds of the invention have pharmacological activity as shown by the following pharmacological tests; the reference substance chosen was vincamine.

ACUTE TOXICITY

The compounds of the invention were administered intraperitoneally to mice of the strain CD1. The mortality was recorded for 7 days and the 50% lethal doses ($LD_{50}$) were determined graphically.

ANOXIA TEST ON MICE UNDER LOW (OXYGEN) PRESSURE CONDITIONS

Mice of the CD1 strain are kept in an atmosphere depleted in oxygen, by producing a partial vacuum (190 mm of mercury, corresponding to 5.25% of oxygen).

The survival time of the animals is noted. This time is increased by agents capable of assisting tissue oxygenation and in particular cerebal oxygenation. The compounds studied are administered in several doses intraperitoneally 10 minutes before the test. The percentage increases in the survival time relative to the values obtained with comparison animals are calculated. The mean active dose (MAD), the dose which increases the survival time by 100%, is determined graphically.

The effects obtained with the compounds of the invention were compared with those of vincamine. By way of example, the results obtained for the compound of Example 1 (SL C 072) are summarised in Table 1.

TABLE 1

| Compound of Example | Acute toxicity $LD_{50}$(mg/kg) Intraperitoneal | Oral | Protective activity in the anoxia test under reduced pressure conditions, MAD, mg/kg administered intraperitoneally (expressed as the base) |
|---|---|---|---|
| 1 | 430 | 2100 | 5.5 |
| 3 | 440 | 2800 | 5 |
| Vincamine | 215 | 460 | 8 |

The compounds of Examples 1 and 3 furthermore possess vasodilating properties which are high in respect of both intensity and duration; the intensity of this vasodilating activity on the flow in the femoral artery of dogs was evaluated to be three times that of papaverine administered at the same dose (expressed as the base). Furthermore, the vasodilating effect obtained was 2 to 3 times more lasting than that of papaverine.

According to these tests, the compounds of Examples 1 and 3, which are the preferred compounds of the invention have:
- an anti-anoxia activity which is markedly greater than that of vincamine.
- a toxicity which, compared to that of vincamine, is lower by a factor of 2 when administered intraperitoneally and lower by a factor of about 5 when administered orally, and
- a vasodilating activity which, relative to that of papaverine, is 3 times greater and lasts 2 to 3 times longer.

This latter activity makes the two compounds in question particularly interesting because vincamine and its known derivatives have a vasodilating activity which is at most equal to that of papaverine.

The compounds of the invention are thus valuable for use in therapy in human and veterinary medicine, especially in the field of cardiac-circulatory insufficiencies, cerebralvascular insufficiencies or respiratory insufficiencies.

The invention therefore provides pharmaceutical compositions comprising the compounds of general formula (I) and/or an acid addition salt thereof and a pharmaceutically acceptable carrier or diluent. The compositions are preferably in a form suitable for oral or parenteral administration; they can also contain other medicinal substances with which the compounds of general formula (I) are pharmacologically and therapeutically compatible. The invention also provides pharmaceutical compositions containing the compounds of general formula (I) and/or their salts together with ascorbic acid, either in the form of the free acid or in the form of one of its known salts or in the form of a complex such as an equimolecular complex of ascorbic acid with nicotinamide or an equimolecular complex of ascorbic acid with pyridoxine, these compositions having the advantage of permitting better resorption of the compounds of general formula (I) by the digestive tract.

For oral administration, all the usual forms appropriate for this method can be employed; examples are tablets, dragees, pills, capsules, cachets and potable solutions or suspensions, in which the unit weight of active principle can be 0.5 to 25 mg and the daily dose can be 0.5 to 100 mg.

For parenteral administration, solutions prepared beforehand or immediately prior to use and buffered to a physiological pH can be employed. These solutions can contain 0.5 to 20 mg of active principle in a volume of 1 to 5 ml. Usually the solution is divided into ampoules of 1 to 5 ml capacity for intramuscular or intravenous injection, or for administration by slow intravenous infusion. The daily dose for parenteral administration can be 0.5 to 100 mg.

We claim:

1. A compound which has the general formula (I)

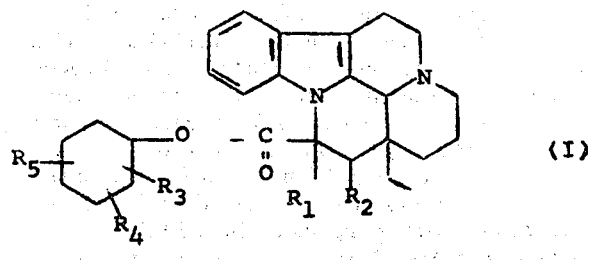

wherein
 R₁ is a hydrogen atom or a hydroxy group,
 R₂ is a hydrogen atom or
 R₁ and R₂ together form an additional bond between the two carbon atoms to which they are attached, and each of R₃, R₄ and R₅ which may be the same or different is a hydrogen atom or a methyl group, or a pharmaceutically acceptable acid addition salt thereof with an inorganic or organic acid.

2. A compound as claimed in claim 1 wherein R₃ and R₄ are methyl groups in the 3-position and R₅ is a methyl group in the 5-position, or a salt thereof.

3. A compound as claimed in claim 1 which is 3,3,5-trimethylcyclohexyl apovincaminate.

4. A salt as claimed in claim 1 which is the hydrochloride of 3,3,5-trimethylcyclohexyl apovincaminate.

5. A salt as claimed in claim 1 which is the methanesulphonate of 3,3,5-trimethylcyclohexyl apovincaminate.

6. A compound according to claim 1 which is 3,3,5-trimethylcyclohexyl desoxyvincaminate.

7. A salt as claimed in claim 1 which is the hydrochloride of 3,3,5-trimethylcyclohexyl desoxyvincaminate.

8. A pharmaceutical composition suitable for treating cardiac-circulatory cerebral-vascular or respiratory insufficiency in mammals consisting essentially of an effective amount of at least one compound or salt of claim 1, and a pharmaceutically acceptable carrier or diluent.

9. A composition as claimed in claim 8 containing also ascorbic acid or a salt or complex thereof.

10. A composition as claimed in claim 9 wherein the complex is either an equimolecular complex of ascorbic acid with nicotinamide or an equimolecular complex of ascorbic acid with pyridoxine.

11. A composition according to claim 9 wherein the weight ratio of the compound of general formula (I) to ascorbic acid is 4:1 to 1:200.

12. A composition according to claim 11 wherein the ratio is 2:1 to 1:5.

13. A method of treating cardiac-circulatory cerebral-vascular and/or respiratory insufficiency in mammals, the method consisting essentially of administering to the mammal an effective amount of a compound or salt according to claim 1.

* * * * *